(12) United States Patent
Livant

(10) Patent No.: US 7,320,783 B2
(45) Date of Patent: Jan. 22, 2008

(54) METHODS AND COMPOSITIONS FOR THE ENHANCEMENT OF WOUND HEALING

(75) Inventor: Donna L. Livant, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 735 days.

(21) Appl. No.: 10/619,809

(22) Filed: Jul. 15, 2003

(65) Prior Publication Data
US 2004/0096438 A1    May 20, 2004

Related U.S. Application Data

(60) Provisional application No. 60/396,366, filed on Jul. 17, 2002.

(51) Int. Cl.
*A61K 51/00* (2006.01)
*A61M 36/14* (2006.01)

(52) U.S. Cl. .................. 424/1.69; 424/1.11; 424/1.65; 424/9.1; 206/223; 514/2

(58) Field of Classification Search ............... 424/1.11, 424/1.65, 1.69, 9.1; 206/223, 569, 570; 514/2, 514/9
See application file for complete search history.

(56) References Cited

U.S. PATENT DOCUMENTS 5,175,343 A * 12/1992 Fritzberg et al. ............ 560/145

* cited by examiner

*Primary Examiner*—Dameron L. Jones
(74) *Attorney, Agent, or Firm*—Medlen & Carroll, LLP

(57) ABSTRACT

The present invention relates to methods and compositions for wound healing, and in particular, methods and compositions to promote and enhance wound healing. In particular, the present invention provides MMP derived peptides for use in enhancing wound healing.

8 Claims, 7 Drawing Sheets

SEQUENCE LISTING

<160> NUMBER OF SEQ ID NOS: 11

<210> SEQ ID NO 1
<211> LENGTH: 11
<212> TYPE: PRT
<213> ORGANISM: Homo sapiens

```
<400> SEQUENCE: 1

Pro Arg Cys Gly Val Pro Asp Val Ala Gln Phe
1               5                   10

<210> SEQ ID NO 2
<211> LENGTH: 11
<212> TYPE: PRT
<213> ORGANISM: Homo sapiens

<400> SEQUENCE: 2

Pro Arg Cys Gly Val Pro Asp Val Ala Glu Tyr
1               5                   10

<210> SEQ ID NO 3
<211> LENGTH: 11
<212> TYPE: PRT
<213> ORGANISM: Homo sapiens

<400> SEQUENCE: 3

Pro Arg Cys Gly Asn Pro Asp Val Ala Asn Tyr
1               5                   10

<210> SEQ ID NO 4
<211> LENGTH: 12
<212> TYPE: PRT
<213> ORGANISM: Homo sapiens

<400> SEQUENCE: 4

Pro Arg Cys Gly Val Pro Asp Leu Gly Arg Phe Gln
1               5                   10

<210> SEQ ID NO 5
<211> LENGTH: 5
<212> TYPE: PRT
<213> ORGANISM: Homo sapiens

<400> SEQUENCE: 5

Pro His Ser Arg Asn
1               5

<210> SEQ ID NO 6
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: This residue can be Valine or Asparagine.

<400> SEQUENCE: 6

Pro Arg Cys Gly Xaa Pro Asp Val Ala
1               5

<210> SEQ ID NO 7
<211> LENGTH: 11
<212> TYPE: PRT
<213> ORGANISM: Homo sapiens

<400> SEQUENCE: 7

Pro Arg Ser Gly Val Pro Asp Val Ala Gln Phe
1               5                   10
```

```
<210> SEQ ID NO 8
<211> LENGTH: 11
<212> TYPE: PRT
<213> ORGANISM: Homo sapiens

<400> SEQUENCE: 8

Pro Arg Ser Gly Val Pro Asp Val Ala Glu Tyr
1               5                   10

<210> SEQ ID NO 9
<211> LENGTH: 11
<212> TYPE: PRT
<213> ORGANISM: Homo sapiens

<400> SEQUENCE: 9

Pro Arg Ser Gly Asn Pro Asp Val Ala Asn Tyr
1               5                   10

<210> SEQ ID NO 10
<211> LENGTH: 12
<212> TYPE: PRT
<213> ORGANISM: Homo sapiens

<400> SEQUENCE: 10

Pro Arg Ser Gly Val Pro Asp Leu Gly Arg Phe Gln
1               5                   10

<210> SEQ ID NO 11
<211> LENGTH: 11
<212> TYPE: PRT
<213> ORGANISM: Homo sapiens

<400> SEQUENCE: 11

Val Val Asp Ala Pro Pro Phe Cys Gly Gln Arg
1               5                   10
```

METHODS AND COMPOSITIONS FOR THE ENHANCEMENT OF WOUND HEALING

The present invention claims priority to U.S. Provisional Patent Application Ser. No. 60/396,366, filed Jul. 17, 2002, the disclosure of which is herein incorporated by reference in its entirety.

FIELD OF THE INVENTION

The present invention relates to methods and compositions for wound healing, and in particular, methods and compositions to promote and enhance wound healing.

BACKGROUND

The primary goal in the treatment of wounds is to achieve wound closure. Open cutaneous wounds represent one major category of wounds and include burn wounds, neuropathic ulcers, pressure sores, venous stasis ulcers, and diabetic ulcers. Open cutaneous wounds routinely heal by a process which comprises six major components: i) inflammation, ii) fibroblast proliferation, iii) blood vessel proliferation, iv) connective tissue synthesis v) epithelialization, and vi) wound contraction. Wound healing is impaired when these components, either individually or as a whole, do not function properly. Numerous factors can affect wound healing, including malnutrition, infection, pharmacological agents (e.g., actinomycin and steroids), diabetes, and advanced age [see Hunt and Goodson in *Current Surgical Diagnosis & Treatment* (Way; Appleton & Lange), pp. 86-98 (1988)].

With respect to diabetes, it is known that delayed wound healing causes substantial morbidity in patients with diabetes. Diabetes mellitus is a chronic disorder of glucose metabolism and homeostasis that damages many organs. It is the eighth leading cause of death in the United States (Harris et al., *Diabetes* 36:523 (1987)). In persons with diabetes, vascular disease, neuropathy, infections, and recurrent trauma predispose the extremities, especially the foot, to pathologic changes. These pathological changes can ultimately lead to chronic ulceration, which may necessitate amputation.

The most commonly used conventional modality to assist in wound healing involves the use of wound dressings. In the 1960s, a major breakthrough in wound care occurred when it was discovered that wound healing with a moist occlusive dressings was, generally speaking, more effective than the use of dry, non-occlusive dressings [Winter, *Nature* 193:293-94 (1962)]. Today, numerous types of dressings are routinely used, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer) [Kannon and Garrett, Dermatol. Surg. 21:583-590 (1995); Davies, *Burns* 10:94 (1983)]. Unfortunately, certain types of wounds (e.g., diabetic ulcers, pressure sores) and the wounds of certain subjects (e.g., recipients of exogenous corticosteroids) do not heal in a timely manner (or at all) with the use of such dressings.

Several pharmaceutical modalities have also been utilized in an attempt to improve wound healing. For example, treatment regimens involving zinc sulfate have been utilized by some practitioners. However, the efficacy of these regimens has been primarily attributed to their reversal of the effects of sub-normal serum zinc levels (e.g., decreased host resistance and altered intracellular bactericidal activity) [Riley, *Am. Fam. Physician* 24:107 (1981)]. While other vitamin and mineral deficiencies have also been associated with decreased wound healing (e.g., deficiencies of vitamins A, C and D; and calcium, magnesium, copper, and iron), there is no strong evidence that increasing the serum levels of these substances above their normal levels actually enhances wound healing. Thus, except in very limited circumstances, the promotion of wound healing with these agents has met with little success.

What is needed is a safe, effective, and interactive means for enhancing the healing of wounds of all types and without regard to the type of wound or the nature of the patient population to which the subject belongs.

SUMMARY OF THE INVENTION

The present invention relates to methods and compositions for wound healing, and in particular, methods and compositions to promote and enhance wound healing. For example, in some embodiments, the present invention provides a method for treating a wound, comprising providing an MMP prodomain peptide, and a subject having at least one wound; and administering the peptide to the subject under conditions such that the healing of the wound is promoted. In some embodiments, the subject is a patient with diabetes. In other embodiments, the subject is a burn patient. In still further embodiments, the wound is a chronic wound. In some embodiments, the peptide is derived from MMP 1 (e.g., including, but not limited to, a peptide with the amino acid sequence Ac-PRCGVPDVAQF-NH$_2$ (SEQ ID NO:1 )). In other embodiments, the peptide is derived from MMP 7 (e.g., including, but not limited to, a peptide with the amino acid sequence Ac-PRCGVPDVAEY-NH$_2$ (SEQ ID NO:2)). In still further embodiments, the peptide is derived from MMP 2 (e.g., including, but not limited to, a peptide with the amino acid sequence Ac-PRCGNPDVANY-NH$_2$ (SEQ ID NO:3)). In yet other embodiments, the peptide is derived from MMP 9 (e.g., including, but not limited to, a peptide with the amino acid sequence Ac-PRCGVPDLGRFQ-NH$_2$ (SEQ ID NO:4)).

The present invention further provides a kit for the treatment of wounds in a subject, comprising an MMP prodomain peptide; and instructions for using the peptide to treat wounds in the subject. In some embodiments, the subject is a patient with diabetes. In other embodiments, the subject is a burn patient. In still further embodiments, the wound is a chronic wound. In some embodiments, the peptide is derived from MMP 1 (e.g., including, but not limited to, a peptide with the amino acid sequence Ac-PRCGVPDVAQF-NH$_2$ (SEQ ID NO:1 )). In other embodiments, the peptide is derived from MMP 7 (e.g., including, but not limited to, a peptide with the amino acid sequence Ac-PRCGVPDVAEY-NH$_2$) (SEQ ID NO:2). In still further embodiments, the peptide is derived from MMP 2 (e.g., including, but not limited to, a peptide with the amino acid sequence Ac-PRCGNPDVANY-NH$_2$ (SEQ ID NO:3)). In yet other embodiments, the peptide is derived from MMP 9 (e.g., including, but not limited to, a peptide with the amino acid sequence Ac-PRCGVPDLGRFQ-NH$_2$ (SEQ ID NO:4)).

GENERAL DESCRIPTION OF THE INVENTION

Figure 1:
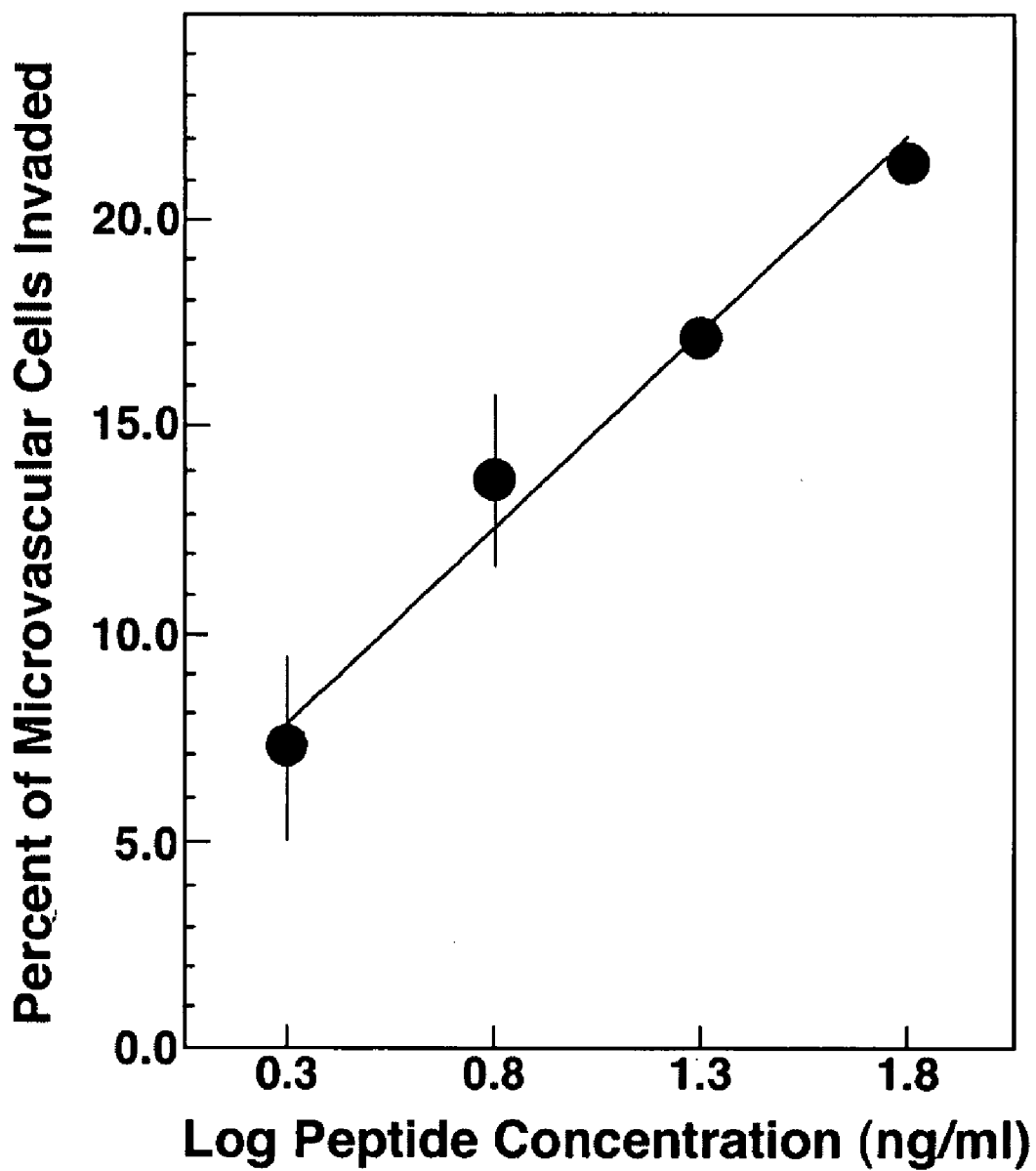
FIG. 1 shows induction of human microvascular cell invasion by the MMP 7 switch peptide, Ac-PRCGVPD- VAEY-NH$_2$ (SEQ ID NO:2). X axis, log of the peptide concentration in ng/ml. The peptide concentrations used are as follows: 2, 6, 20, and 60 ng/ml. Y axis, percent of microvascular cells invaded. Means are shown with first standard deviations.

Patients with diabetes exhibit delayed wound healing because of changes in vascular basement membranes and extracellular matrix that are believed to delay the entry of cells into wounds (Williamson et al., (1988) Diab. Metabol. Rev. 4: 339-370). As a result of impaired wound healing, diabetics often encounter considerable difficulties in healing ulcers and controlling infection, especially in the lower extremities. A portion of these slowly-healing wounds can become chronic, and necessitate amputation (Pierce, (2001) Am. J. Pathol. 159: 399-403). Topical agents that can induce the invasion of wound provisional matrix by surrounding fibroblasts and microvascular cells, and accelerate closure by stimulating epithelial cell migration across the provisional matrix surface could have significant therapeutic value in speeding wound healing, reducing the chances of infection, and thereby preventing the development of chronic, non-healing wounds, whether used alone or in combination with agents to control infection. Although not curative of the diabetes, these topical agents would thus make it much easier for patients to live with their disease.

The C57BL6Ks db/db mouse has been used extensively as a model of diabetic wounds in humans (Coleman, (1982) Diabetes 31:1-6.). This mouse strain has a leptin receptor deficiency caused by a specific point mutation that affects splicing (Lee et al., (1996) Nature 379: 632-635). db/db mouse wounds have been shown to have a number of molecular features in common with human diabetic wounds. For example, the wounds of db/db mice exhibit a decreased influx of inflammatory cells, as well as reduced growth factor expression (Fahey et al., (1991) J. Surg. Res. 50: 308-313; Werner et al., (1994) J. Invest. Dermatol. 103: 469-473). The demonstration that impaired healing in db/db mice could be reversed by the topical application of polypeptide growth factors, including fibroblast growth factor-2 (FGF-2) and platelet-derived growth factor-BB (PDGF-BB) (Tsuboi et al., (1990) J. Exp. Med. 172: 245-251), lead to the successful trial of platelet derived growth factor-BB in human diabetics (Smiell et al., (1999) Wound Repair Regen. 7: 335-346). Also, the PHSRN (SEQ ID NO:5) sequence of the fibronectin cell-binding domain has been shown to induce α5β1 integrin fibronectin receptor-mediated fibroblast and keratinocyte invasion of the extracellular matrix in vitro, as well as stimulate the rapid reepithelialization and contraction of dermal wounds in db/db mice, when applied as a peptide, Ac-PHSRN-NH$_2$ (Livant et al., (2000) J. Clin. Invest. 105: 1537-1545). The successful completion of reepithelialization in this impaired wound healing model has been interpreted as indicating avoidance of the destructive matrix metalloproteinase expression profile that limits closure and can result in chronic, non-healing wounds (Neely et al., (2000) J. Burn Care & Rehab. 21: 395-402). Thus, many investigators have found the C57BL6Ksdb/db mouse strain to be a very useful model for evaluating the effects of topically added polypeptides on healing-impaired wounds, and predicting their effects in the wounds of human diabetics.

Matrix metalloproteinases are a large family of zinc proteinases that are secreted by both resident and inflammatory cells. Collectively, they are capable of remodeling or degrading virtually all of the molecules of the extracellular matrix. This processing of the extracellular matrix is crucial for wound healing and angiogenesis, as well as for development, differentiation, cell migration, and tumor cell metastasis. Interstitial collagenase, or MMP-1, is very important in wound healing because this metalloproteinase has been shown to play important roles in reepithelialization, formation of the provisional matrix, and angiogenesis. The triple helical structure of fibrillar collagen makes it very resistant to proteolysis, and only a very limited number of MMPs, including MMP-1 or interstitial collagenase, can cleave it (Stricker et al., (2001) J. Biol. Chem. 276: 29375-29381).

Many experimental findings indicate the importance of MMP-1 activity in reepithelialization. MMP-1 is expressed by keratinocytes migrating on collagen (Pilcher et al., (1997) J. Cell Biol. 137: 1445-1457). Its accumulation has been shown to be stimulated by the interaction of the invasion-inducing, PHSRN (SEQ ID NO:5) sequence of the fibronectin cell-binding domain with the α5β1 integrin fibronectin receptor in normal epithelial cells and in their metastatic counterparts, as well as in fibroblasts (Livant et al., (2000) Cancer Res. 60: 309-320; Livant et al., (2000) J. Clin. Invest. 105: 1537-1545). After secretion, MMP-1 has been shown to interact with the surface α2β1 integrin of keratinocytes during their migration on type I collagen (Dumin et al., (2001) J. Biol. Chem. 276: 29368-29374). Also, MMP-1 has been shown to be substantially upregulated in motile keratinocytes at the leading edge of the new epithelium of wounds, and to be required for successful reepithelialization (Saarialho-Kere et al., (1995) J. Invest. Dermatol. 104: 982-988; Agren et al., Exp. Derm. 10: 337-348). Total MMP-1 activity has been shown to increase approximately 100-fold in the wounded skin of healthy human volunteers, relative to unwounded skin (Petri et al., (1997) Exp. Dermatol. 6: 133-139).

MMP-1 expression is also important in the formation of granulation tissue. Cultured granulation tissue fibroblasts from human volunteers have been found to expressed greatly increased levels of MMP-1 mRNA (Petri et al., (1997) Exp. Dermatol. 6: 133-139). MMP-1 transcription has been found to be upregulated in human dermal fibroblasts in response to wounding (Abe et al., (2001) Eur. J. Dermatol. 11: 112-116). Also, PDGF-BB, a growth factor that stimulates dermal wound healing in both humans and db/db mice (Tsuboi, R. and Rifkin, D. B. (1990) J. Exp. Med. 172: 245-251; Smiell et al., (1999) Wound Repair Regen. 7: 335-346), has been found to consistently up regulate MMP-1 expression in human fibroblasts (Tan et al., (1995) Biochem. J. 310: 585-588).

Many studies also indicate that MMP-1 activity is important in angiogenesis, both in vitro and in vivo. For example, MMP-1 has been shown to be required for angiogenesis by human umbilical vein endothelial cells in collagen gels (Fisher et al. (1994) Dev. Biol. 162: 499-510). Also, microvascular endothelial cells overexpressing FGF-1 have been shown to have a greatly enhanced migration rate through collagen I matrices that depends on MMP-1 activity (Partridge et al., (2000) J. Cell. Biochem. 78: 487-499). Immunofluorescent staining has also shown that MMP-1 is upregulated in early microvessels, as well as in microvessels involved in elongation and spout formation, in cultured human fetal skin (Karelina et al., (1995) J. Invest. Dermatol. 105: 411-417). In addition, deficient MMP-1 activation has been shown to contribute significantly to aging-impaired angiogenesis in humans (Reed et al., (2000) J. Cell Biochem. 77: 116-126).

Thus, the induction and activation of metalloproteinases, in particular MMP-1, are very important processes for wound reepithelialization, provisional matrix formation and maturation, and angiogenesis. The development of topical agents to stimulate these processes is very useful in promoting wound healing and preventing the development of non-healing wounds in diabetic patients. In some embodiments, based on the importance of MMP-1 activity in reepithelialization, provisional matrix formation, and angiogenesis, the present invention provides peptide agents that promote the activation of MMP-1 in fibroblasts and endothelial cells, as well as in keratinocytes, to promote the closure of dermal wounds in obese diabetic mice. Experiments conducted during the course of development of the present invention demonstrated that peptides containing the highly conserved MMP prodomain cysteine switch region are potent inducers of invasion, that this invasion depends specifically on MMP-1 activity, and that it is not α5β1-mediated. While the present invention is not limited to any mechanism and an understanding of the mechanism is not necessary to practice the present invention, it is contemplated that the effect is the result of a pathway independent of PHSRN-induced invasion since the PHSRN sequence has been shown to interact only with α5β1 (Aota, S., Nagai, T., and Yamada, K. M. (1991) Biol. Chem. 266: 15938-15943). Further experiments demonstrated that a single topical application of a peptide containing the MMP prodomain cysteine switch region enhances db/db wound healing, making wound contraction and closure at least as rapid as that observed in untreated, normally healing, db/+ littermates.

It has long been known that MMPs are expressed as latent proenzymes, which must be activated by proteolytic cleavage of the prodomain, and that a highly conserved cysteine at a constant position in the prodomain, called the cysteine switch, functions in activation. This cysteine has been shown to coordinate with a zinc cation at the active site, thereby preventing hydration of the cation and subsequent proteolytic activation (Springman et al., (1990) Proc. Natl. Acad. Sci. 87: 364-368; Morgunova et al., (1999) Science 284: 1667-1669). Latent forms of MMPs can be activated by a variety of treatments affecting the cysteine switch (Springman et al., (1990) Proc. Natl. Acad. Sci. 87: 364-368; Morgunova et al., (1999) Science 284: 1667-1669). Experiments conducted during the course of development of the present invention demonstrated that exposure to the conserved cysteine switch region of the cleaved propeptide can activate MMP 1 to induce invasion and enhance diabetic wound healing.

Definitions

To facilitate understanding of the invention set forth in the disclosure that follows, a number of terms are defined below.

The term "wound" refers broadly to injuries to the skin and subcutaneous tissue initiated in different ways (e.g., pressure sores from extended bed rest and wounds induced by trauma) and with varying characteristics. Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The term "partial thickness wound" refers to wounds that encompass Grades I-III; examples of partial thickness wounds include burn wounds, pressure sores, venous stasis ulcers, and diabetic ulcers. The term "deep wound" is meant to include both Grade mi and Grade IV wounds. The present invention contemplates treating all wound types, including deep wounds and chronic wounds.

The term "chronic wound" refers to a wound that has not healed within 30 days.

The phrases "promote wound healing," "enhance wound healing," and the like refer to either the induction of the formation of granulation tissue of wound contraction and/or the induction of epithelialization (i.e., the generation of new cells in the epithelium). Wound healing is conveniently measured by decreasing wound area.

The phrase "wound fluid contents" refers to liquid associated with a wound, as well as cells, cell factors, ions, macromolecules and protein material suspended such liquid at the wound site.

The term "subject" refers to both humans and animals.

The terms "enclosure," "compartment," and the like refer broadly to any container capable of confining a solid support within a defined location.

The term "solid support" refers broadly to any support, including, but not limited to, microcarrier beads, gels, BAND-AIDS and dressings.

The term "dressing" refers broadly to any material applied to a wound for protection, absorbance, drainage, etc. Thus, adsorbent and absorbent materials are specifically contemplated as a solid support. Numerous types of dressings are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer) [Kannon and Garrett, *Dermatol. Surg.* 21:583-590 (1995); Davies, *Burns* 10:94 (1983)]. The present invention specifically contemplates the use of dressings impregnated with the wound healing promoting and enhancing compounds of the present invention.

The term "biocompatible" means that there is minimal (i.e., no significant difference is seen compared to a control), if any, effect on the surroundings. For example, in some embodiments of the present invention, the dressing comprises a biocompatible membrane.

The term "peptide derivative" refers to compound having an imino group (—NH—), and more particularly, a peptide bond. Peptides may be regarded as substituted amides. Like the amide group, the peptide bond shows a high degree of resonance stabilization. The C—N single bond in the peptide linkage has typically about 40 percent double-bond character and the C═O double bond about 40 percent single-bond character.

"Protecting groups" are those groups that prevent undesirable reactions (such as proteolysis) involving unprotected functional groups. In one embodiment, the present invention contemplates that the protecting group is an acyl or an amide. In one embodiment, the acyl is acetate. In another embodiment, the protecting group is a benzyl group. In another embodiment, the protecting group is a benzoyl group. The present invention also contemplates combinations of such protecting groups.

DETAILED DESCRIPTION OF THE INVENTION

Rapid induction of fibroblast, keratinocyte, and endothelial cell migration into dermal wounds is crucial for successful tissue repair. Interstitial collagenase or MMP-1 is a key feature of healing wounds because it has been shown to function in reepithelialization, formation of the provisional matrix, and angiogenesis. Active MMP-1 is associated with keratinocytes, as they migrate across the surface of the provisional matrix. It is also associated with fibroblasts during invasion of the provisional matrix. Finally, it is associated with the invading sprouts of capillaries as they invade the extracellular matrix of the wound during angiogenesis. MMPs are expressed as latent proenzymes, that must be activated by proteolytic cleavage of their pro-domains. A highly conserved cysteine, corresponding to $C^{73}$ of MMP-1, is found at a constant position in the prodomain, functions in activation. This cysteine residue is called the cysteine switch because it coordinates with the zinc cation of the active site in the proprotein, thus preventing the hydration of the zinc cation and blocking the active site. During MMP activation, cleavage of the prodomain removes the cysteine switch, and allows hydration of the active site zinc cation, thus making the active site accessible to substrate collagen.

A method for activating the cysteine switch of MMP-1 is needed. The present invention is not limited to a particular mechanism. Indeed, an understanding of the mechanism is not necessary to practice the present invention. Nonetheless, it is contemplated that, because compounds that can induce the local conversion of proenzyme to active MMP-1 in epithelial cells, fibroblasts and microvascular endothelial cells are contemplated to be potent topical agents for promoting wound healing. These agents are especially useful in diabetic patients because the cellular invasion of diabetic wounds is known to contribute to their impaired healing. In addition to the therapeutic potential of these peptide agents to alleviate some of the worst consequences of diabetic disease, i.e. the development of chronic wounds in the extremities that can lead to amputation, the present invention provides peptides containing the highly conserved cysteine switch regions of MMP prodomains for use as potent stimulators of MMP-1 activity, and thus of extracellular matrix invasion by keratinocytes, fibroblasts, and endothelial cells. The present invention further provides methods of using topical application of MMP cysteine switch-containing peptides to cure the diabetic defect in wound closure in db/db mice by stimulating reepithelialization, provisional matrix formation, and angiogenesis. Thus, in some embodiments, the present invention provides agents capable of stimulating MMP-1 activation to promote reepithelialization, provisional matrix formation, and angiogenesis.

I. Peptides

In some embodiments, the present invention provides peptides derived from MMP proteins. The present invention is not limited to peptides derived from a particular MMP protein. Peptides and mimetics (See section II below) derived from a variety of MMP proteins including, but not limited to, MMP 1, MMP 2, MMP 7, and MMP 9 are contemplated. As described above, it is contemplated that peptides comprising cysteine switch sequences are particularly preferred for use in the compositions and methods of the present invention. Exemplary peptide sequences include, but are not limited to, Ac-PRCGVPDVAQF-NH$_2$ (SEQ ID NO:1) (MMP 1 prodomain peptide), Ac-PRCGVPDVAEY-NH$_2$ (SEQ ID NO:2) (MMP 7), Ac-PRCGNPDVANY-NH$_2$ (SEQ ID NO:3) (MMP2), and Ac-PRCGVPDLGRFQ-NH$_2$ (SEQ ID NO:4) (MMP 9).

The present invention also contemplates the use of variants of any of the specified sequences disclosed herein. Variants include those peptide with conserved amino acid change (e.g., substitution of amino acids with similar charge, size, hydophobicity, etc.), peptide containing additional C-terminal or N-terminal amino acids, as well as other functional equivalents. Functional equivalents can be determined by using simple assays, such as those described in Section III, below.

II. Mimetics

Compounds mimicking the necessary conformation for recognition and docking to the receptor binding to the peptides of the present invention are contemplated as within the scope of this invention. For example, mimetics of the peptides described in Section I above are contemplated. A variety of designs for such mimetics are possible. For example, cyclic peptides, in which the necessary conformation for binding is stabilized by nonpeptides, are specifically contemplated. U.S. Pat. No. 5,192,746 to Lobl, et al, U.S. Pat. No. 5,169,862 to Burke, Jr., et al, U.S. Pat. No. 5,539,085 to Bischoff, et al, U.S. Pat. No. 5,576,423 to Aversa, et al, U.S. Pat. No. 5,051,448 to Shashoua, and U.S. Pat. No. 5,559,103 to Gaeta, et al, all hereby incorporated by reference, describe multiple methods for creating such compounds.

Synthesis of nonpeptide compounds that mimic peptide sequences is also known in the art. Eldred, et al, (*J. Med. Chem.* 37:3882 (1994)) describe nonpeptide antagonists that mimic the Arg-Gly-Asp sequence. Likewise, Ku, et al, (*J. Med. Chem.* 38:9 (1995)) give further elucidation of the synthesis of a series of such compounds. Such nonpeptide compounds that mimic the peptides of the present invention are specifically contemplated by the present invention.

The present invention also contemplates synthetic mimicking compounds that are multimeric compounds that repeat the relevant peptide sequence. In one embodiment of the present invention, it is contemplated that the relevant peptide sequence is PRCGV/NPDVA (SEQ ID NO:6) sequence of the MMP prodomain. As is known in the art, peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the a-amino group of the component containing the activated carboxyl group can be blocked with a tertbutyloxycarbonyl group. This protecting group can be subsequently removed by exposing the peptide to dilute acid, which leaves peptide bonds intact.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

In one embodiment, the mimetics of the present invention are peptides having sequence homology to the above-described peptides (including, but not limited to, peptides in which L-amino acids are replaced by their D-isomers). One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant. W. R. Pearson and D. J. Lipman, *Proc. Natl. Acad. Sci.* (USA), 85:2444-2448 (1988); D. J. Lipman and W. R. Pearson, *Science,* 227:1435-1441 (1985). In the present invention, synthetic polypeptides useful in wound healing are those peptides with statistically significant sequence homology and similarity (Z value of Lipman and Pearson algorithm in Monte Carlo analysis exceeding 6).

III. Assays

In preferred embodiments, candidate peptides and mimetics are screened for their activity in invasion induction, stimulation of activated MMP, and stimulation of wound healing. Any suitable assay may be utilized for such experiments including, but not limited to, those described below.

A. Invasion Induction

In some embodiments, the present invention provides methods of using MMP mimetics for induction of invasion. In some embodiments, candidate peptides of the present invention are assayed for their ability to induce invasion. In some embodiments, invasion induction is quantitated by exposing normal human keratinocytes, fibroblasts, and microvascular cells to peptides, and placed on SU-ECM in vitro invasion substrates. The role of activated MMPs in invasion induction is assessed functionally through the use of the blocking anti-MMP 1 COMY 4A2 antibody (Birkedal-Hansen et al., Biochemistry 27: 6751-6758) with appropriate isotype controls. Blocking anti-MMP 2, and -9 antibodies (Fridman et al., (1992) J. Biol. Chem. 267(22): 15398-15405; Schnaper et al., (1993) J. Cell. Physiol. 156 (2): 235-246.) are also utilized to ascertain if MMP 2 and MMP 9 are also involved in switch peptide-induced invasion.

B. Activation of MMP

Peptides are screened for their ability to stimulate the production of activated MMP (e.g., MMP 1), specifically by affecting the interactions of the cysteine switch of the MMP 1 N-terminal propeptide domain with the active site, peptides in which the cysteine switch amino acid is replaced by serine, will be synthesized. The C-to-S point mutation at this location has been shown to inactivate the cysteine switch in the MMP 1 proprotein (Windsor et al., (1991) Biochem. 30: 641-647). The lack of ability of the C to S peptide to induce invasion of SU-ECM by keratinocytes, fibroblasts, and endothelial cells is verified using SU-ECM in vitro invasion assays, in parallel with assays employing the parental peptide. The role of activated MMP 1 in invasion is assessed functionally on SU-ECM invasion substrates (Livant et al, (1995) *Cancer Res.* 55: 5085-5093) through the use of the blocking anti-MMP 1 COMY 4A2 antibody (Birkedal-Hansen et al., Biochemistry 27: 6751-6758) with appropriate isotype controls. MMP 1 activity is also be quantitated by zymographic analysis of the media from adherent keratinocytes, fibroblasts, and endothelial cells exposed to either the C to S substituted or non-substituted peptides, as described (Livant et al., (2000) J. Clin. Invest. 105: 1537-1545,11). Similar experiments are performed for the switch region peptide from the MMP 7 (Gaire et al., (1994) J. Biol. Chem. 269: 2032-2040), MMP 2 (Huhtala et al., (1990) J. Biol. Chem. 265: 11077-11082), and MMP 9 (Wilhelm et al., (1989) J. Biol. Chem. 264: 17213-17221) prodomains.

C. Wound Healing

Peptides are further evaluated for their ability to stimulate the diabetic wound healing. The peptides are topically applied to duplicate dermal wounds in healing-impaired obese diabetic mice (Greenhalgh et al., (1990) Am. J. Pathol. 136: 1235-1246), according to published protocols (Livant et al., (2000) J. Clin. Invest. 105: 1537-1545). Wound closure times are determined in both treated and untreated mice. To confirm the importance of the cysteine switch residue, some wounds are treated with the C to S substituted peptides. To quantitate the extent of reepithelialization for several days wounding, wounds are excised, sectioned, stained, and examined microscopically. To evaluate the provisional matrix for indications of wound contraction and angiogenesis, the presence of activated fibroblasts, collagenous fibers, microvasculature, and wound macrophages is assessed in sectioned and stained wounds for several days following wounding as described (Livant et al., (2000) J. Clin. Invest. 105: 1537-1545). These assays are performed using peptides derived from MMP 1, MMP 2, MMP 7, and MMP 9.

Experimental

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); 1 or L (liters); ml (milliliters); µl (microliters); cm (centimeters); mm (millimeters); µm (micrometers); nm (nanometers); DS (dextran sulfate); ° C. (degrees Centigrade); and Sigma (Sigma Chemical Co., St. Louis, Mo.).

EXAMPLE 1

The Effect of MMP Peptides on In Vitro Invasion Induction

A. Materials and Methods

About $1 \times 10^5$ human microvascular cells, neonatal fibroblasts, or undifferentiated human keratinocytes were suspended in medium containing 5% fetal calf serum (FCS), mixed with varying concentrations of the MMP 7 switch peptide, Ac-PRCGVPDVAEY-NH$_2$ (Gaire et al., (1994) J. Biol. Chem. 269: 2032-2040), function-blocking anti human MMP 1 monoclonal antibody (Birkedal-Hansen et al., (1988) Biochemistry 27; 6751-6758), or total human IgG, and placed on the surfaces of SU-ECM in vitro invasion substrates. SU-ECM invasion substrates are made as described from sea urchin embryos, and contain a blastocoelic cavity enclosed by an intact basement membrane and associated extracellular matrix (Livant et al., (1995) Cancer Research 55, 5085-5093). After 4 hours of incubation (the time necessary to observe maximal invasion percentages), the invasion percentage in each assay was determined by microscopic examination of the SU-ECM invasion substrates and their associated cells at 400-fold magnification. Invasion percentages are the ratios of the numbers of cells located on the internal surfaces of SU-ECM to the total numbers of cells in contact with either the internal or the external surfaces of SU-ECM, and multiplied by 100.

B. Results

Figure 2:
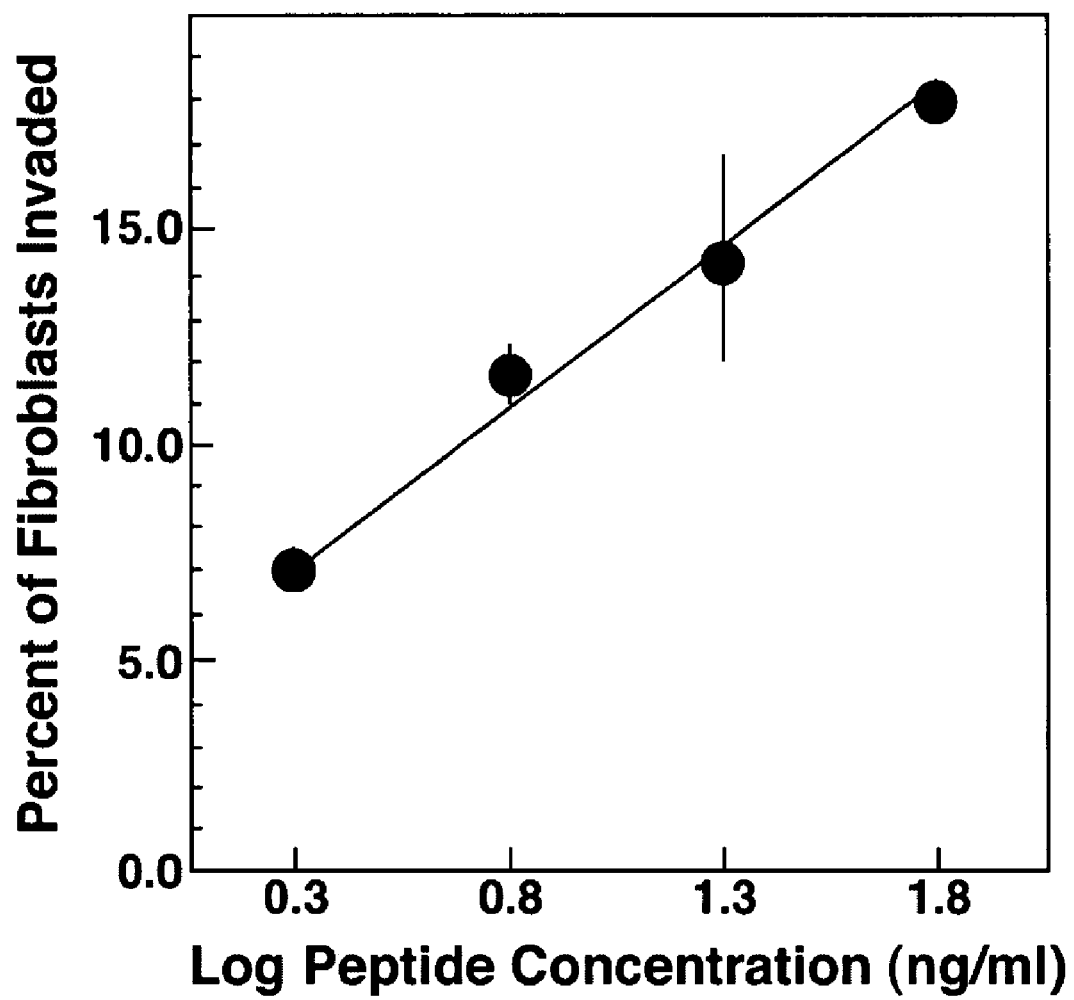
FIG. 2 shows inhibition of Ac-PRCGVPDVAEY-NH$_2$ (SEQ ID NO:2)peptide-induced microvascular cell invasion by blocking anti MMP 1 COMY4A2 monoclonal antibody, but not by total serum IgG. X axis, media constituents: PRC, 600 ng/ml Ac-PRCGVPDVAEY-NH$_2$ (SEQ ID NO:2); COMY4A2, 300 μg/ml anti MMP 1 monoclonal antibody; IgG, 300 μg/ml IgG. Y axis, percentage of invaded microvascular cells relative to the percentage invaded in the presence of 600 ng/ml Ac-PRCGVPDVAEY-NH$_2$ (SEQ ID NO:2) peptide without blocking antibody. Means and first standard deviations are shown.
Figure 3:
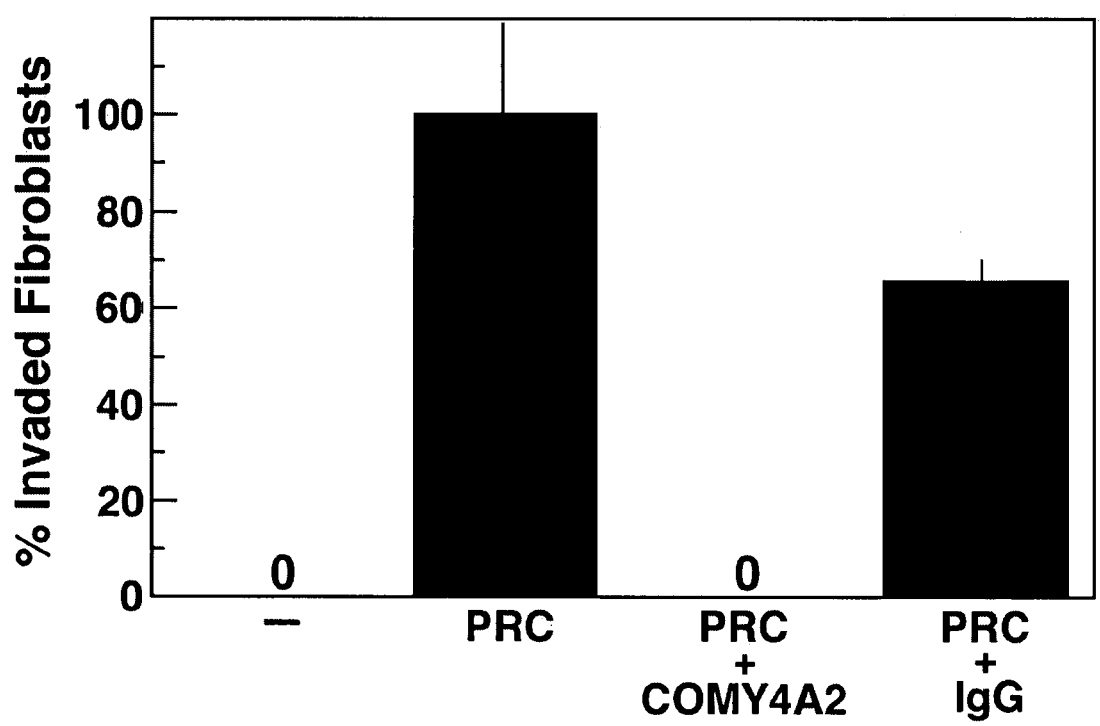
FIG. 3 shows induction of human neonatal fibroblast invasion by the MMP 7 switch peptide, Ac-PRCGVPD-VAEY-NH$_2$ (SEQ ID NO:2). X axis, log of the peptide concentration in ng/ml. The peptide used is the MMP 7 switch peptide, Ac-PRCGVPDVAEY-NH$_2$ (SEQ ID NO:2). The peptide concentrations used are as follows: 2, 6, 20, and 60 ng/ml. Y axis, percent of fibroblasts invaded. Means are shown with first standard deviations.
Figure 4:
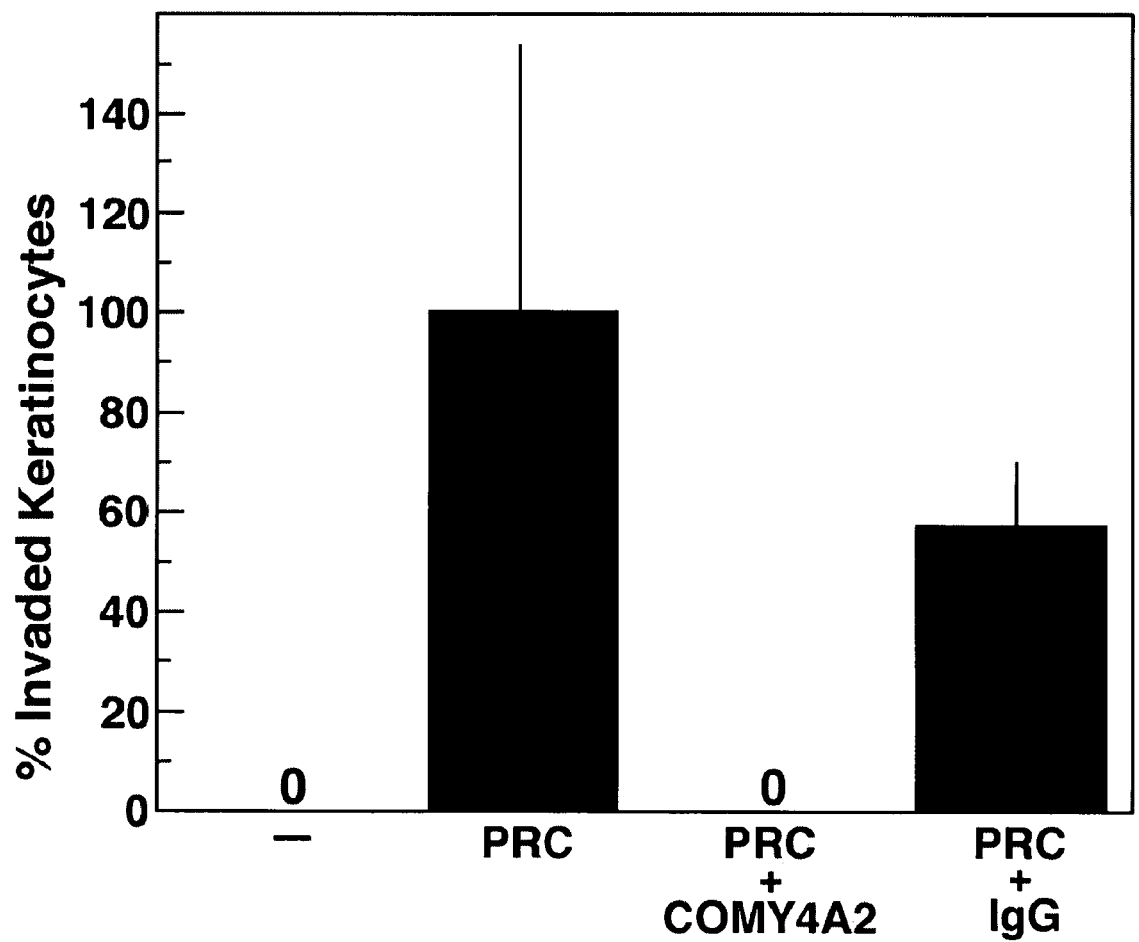
FIG. 4 shows inhibition of Ac-PRCGVPDVAEY-NH$_2$ (SEQ ID NO:2) peptide-induced fibroblast invasion by blocking anti MMP 1 COMY4A2 monoclonal antibody, but not by total serum IgG. X axis, media constitutents: PRC, 600 ng/ml Ac-PRCGVPDVAEY-NH$_2$ (SEQ ID NO:2); COMY4A2, 300 μg/ml anti MMP 1 monoclonal antibody; IgG, 300 μg/ml IgG. Y axis, percentage of invaded fibroblasts relative to the percentage invaded in the presence of 600 ng/ml Ac-PRCGVPDVAEY-NH$_2$ (SEQ ID NO:2) peptide without blocking antibody. Means and first standard deviations are shown.
Figure 5:
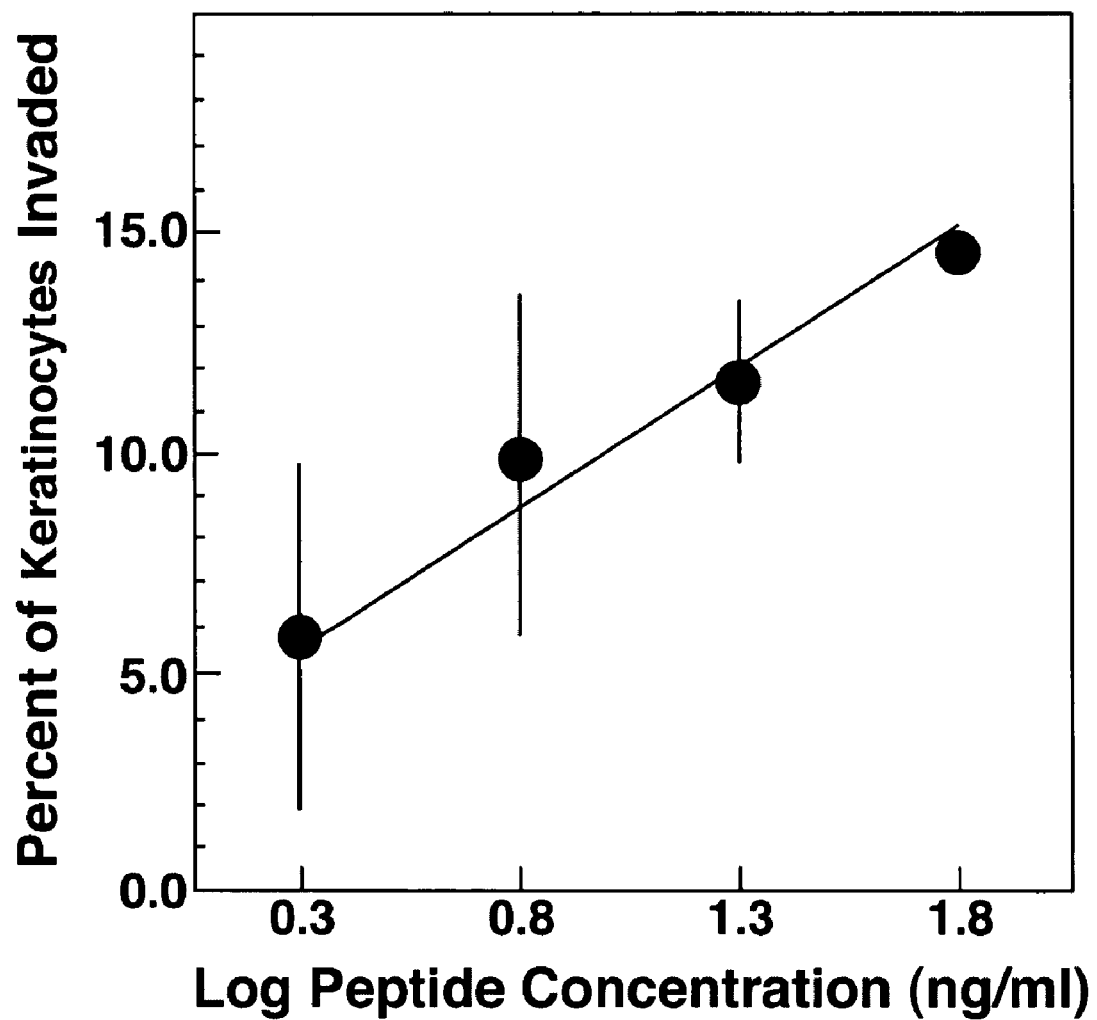
FIG. 5 shows induction of human keratinocyte invasion by the MMP 7 switch peptide, Ac-PRCGVPDVAEY-NH$_2$ (SEQ ID NO:2). X axis, log of the peptide concentration in ng/ml. The peptide used is the MMP 7 switch peptide, Ac-PRCGVPDVAEY-NH$_2$ (SEQ ID NO:2). The peptide concentrations used are as follows: 2, 6, 20, and 60 ng/ml. Y axis, percent of keratinocytes invaded. Means are shown with first standard deviations.
Figure 6:
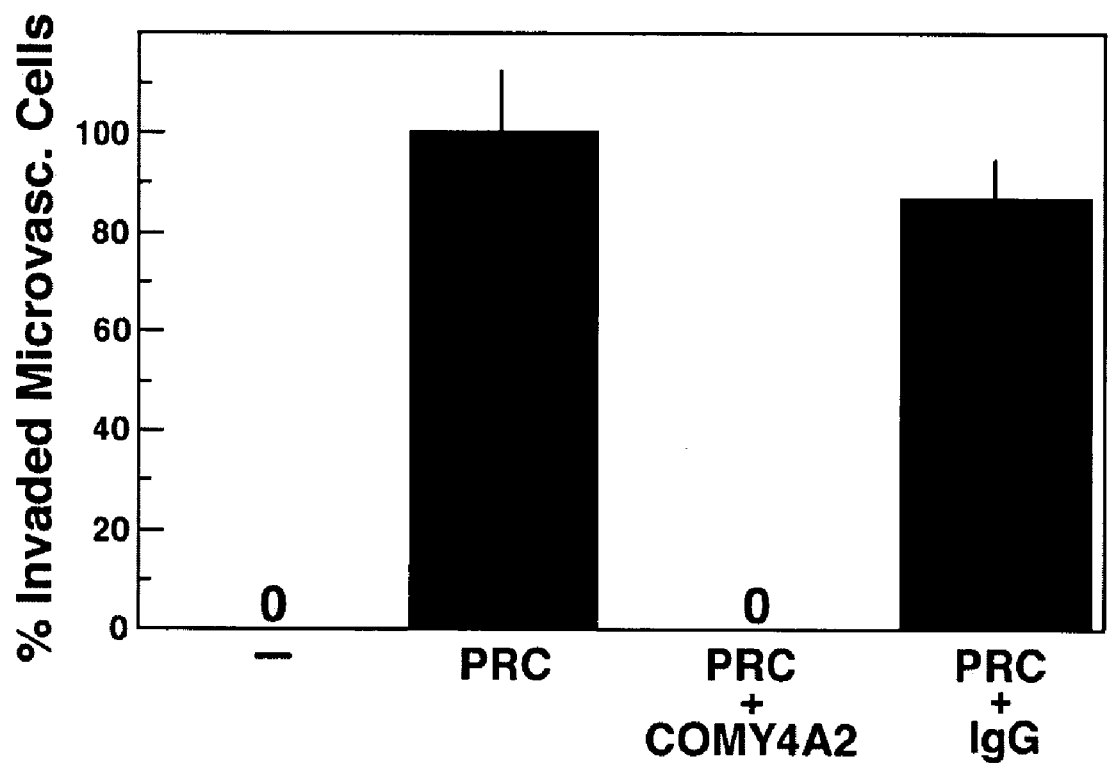
FIG. 6 shows inhibition of Ac-PRCGVPDVAEY-NH$_2$ (SEQ ID NO:2) peptide-induced keratinocyte invasion by blocking anti MMP 1 COMY4A2 monoclonal antibody, but not by total serum IgG. X axis, media constitutents: PRC, 600 ng/ml Ac-PRCGVPDVAEY-NH$_2$ (SEQ ID NO:2); COMY4A2, 300 μg/ml anti MMP 1 monoclonal antibody; IgG, 300 μg/ml IgG. Y axis, percentage of invaded keratinocytes relative to the percentage invaded in the presence of 600 ng/ml Ac-PRCGVPDVAEY-NH$_2$ (SEQ ID NO:2) peptide without blocking antibody. Means and first standard deviations are shown.

The results are shown in FIGS. 1-6. FIG. 1 shows induction of human microvascular cell invasion by the MMP 7 switch peptide, Ac-PRCGVPDVAEY-NH$_2$ (SEQ ID NO:2). The peptide used is the MMP 7 switch peptide, Ac-PRCGVPDVAEY-NH$_2$ (SEQ ID NO:2). The peptide concentrations used are as follows: 2, 6, 20, and 60 ng/ml. FIG. 2 shows that Ac-PRCGVPDVAEY-NH$_2$ (SEQ ID NO:2) peptideinduced microvascular cell invasion is inhibited by blocking anti MMP 1 COMY4A2 monoclonal antibody, but not by total serum IgG. FIG. 3 shows that invasion of human neonatal fibroblasts is enhanced by the MMP 7 switch peptide, Ac-PRCGVPDVAEY-NH$_2$ (SEQ ID NO:2). FIG. 4 shows that Ac-PRCGVPDVAEY-NH$_2$ (SEQ ID NO:2) peptideinduced fibroblast invasion is inhibited by blocking anti MMP 1 COMY4A2 monoclonal antibody, but not by total serum IgG. FIG. 5 shows the induction of human keratinocyte invasion by the MMP 7 switch peptide, Ac-PRCGVPDVAEY-NH$_2$ (SEQ ID NO:2). The peptide used is the MMP 7 switch peptide, Ac-PRCGVPDVAEY-NH$_2$ (SEQ ID NO:2). The peptide concentrations used are as follows: 2, 6, 20, and 60 ng/ml. FIG. 6 shows that Ac-PRCGVPDVAEY-NH$_2$ (SEQ ID NO:2) peptide-induced keratinocyte invasion is inhibited by blocking anti MMP 1 COMY4A2 monoclonal antibody, but not by total serum IgG. In conclusion, the MMP 7 switch peptide induces dose-dependent invasion by human fibroblasts, keratinocytes, and microvascular cells. The inhibition was blocked by a MMP 1-specific monoclonal antibody, but not by serum IgG.

EXAMPLE 2

Enhancement of Wound Healing in Diabetic Mice

A. Methods

Each treatment group consisted of 10 mice with duplicate, dermal wounds of 12.5 to 16.5 mm$^2$ made in the shoulder area. Complete methods were as described (Livant et al., (2000) J. Clin. Invest. 105: 1537-1545). Treated animal were treated with 10 µg switch (PRC) sequence from MMP2 (Ac-PRCGNPDVANY-NH$_2$) (SEQ ID NO:3). Wound areas were measured by integration of digital images.

B. Results

Figure 7:
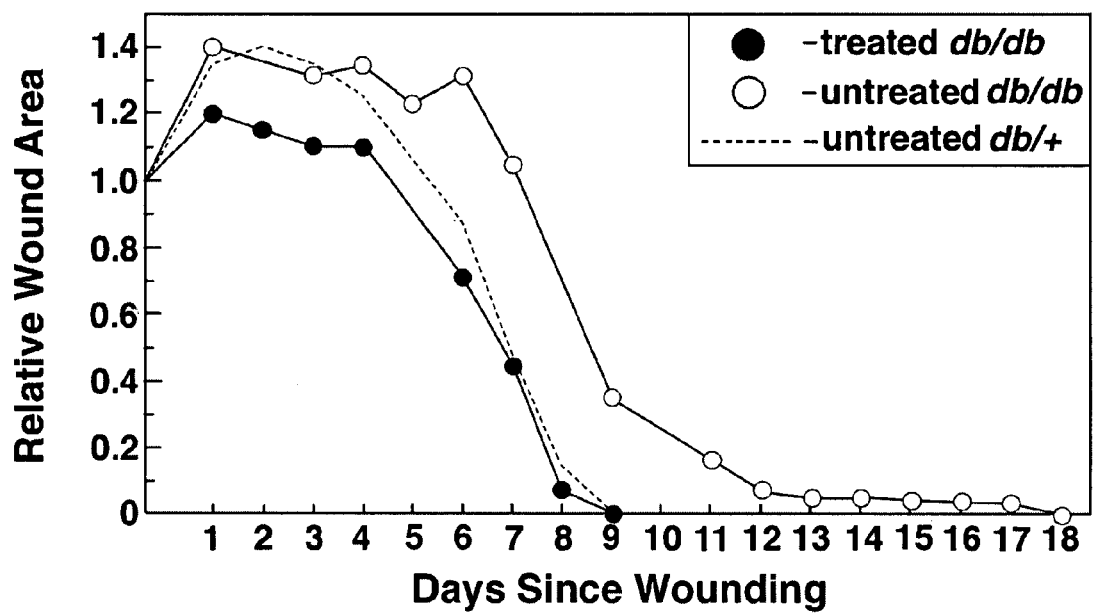
FIG. 7 shows enhancement of C57BL6Ksdb/db obese diabetic mouse wound healing by a topical application of the MMP 2 switch sequence. X axis, days since wounding. Y axis, wound area, relative to the initial wound area (13 to 19 mm$^2$). Db/db: healing-impaired, homozygous db/db, obese diabetic mice; db/+: normally healing, heterozygous db/+, non-diabetic littermates. Mean wound areas are shown.

The results are shown in FIG. 7. One treatment with the PRC peptide just after wounding decreased the time required for closure of all db/db wound by 50%, relative to untreated db/db mice. The closure of PRC-treated wounds appears to be as rapid as that of db/+ non-diabetic mice.

EXAMPLE 3

Methods

This example described methods useful in performing some embodiments of the present invention.

Cell culture and SU-ECM invasion assays. In SU-ECM in vitro invasion substrates, a basement membrane surrounds a blastocoel, in which invading cells localize shortly after suspension and placement on the outer surfaces. Even in the presence of serum, these invasion substrates have been shown to be free of background invasion by normal cells (Livant et al., (1995) *Cancer Res.* 55: 5085-5093; Livant et al., (2000) J. Clin. Invest. 105: 1537-1545; Livant et al., (2000) Cancer Res. 60: 309-320). These invasion substrates have been used to define the invasion-promoting activity of the PHSRN (SEQ ID NO:5) sequence from the fibronectin cellbinding domain, a previously unanticipated function of this sequence. Ac-PHSRN-NH$_2$ (SEQ ID NO:5) peptide has been shown to be a potent topical agent for stimulating dermal wound healing in obese diabetic C57BL6Ksdb/db mice (Livant et al., (2000) J. Clin. Invest. 105: 1537-1545). Because they are naturally serum-free, the SU-ECM invasion substrates have been used to define a potent inhibitor of plasma fibronectin-induced invasion by metastatic prostate cancer cells; and this inhibitor has been shown to be an effective and non-toxic anti-tumorigenic and anti-metastatic agent in Copenhagen rats (Livant et al. (2000) Cancer Res. 60: 309-320), as well as in nude mice bearing human prostate cancer tumors (Windsor et al., (1991) Biochem. 30: 641-647; 38).

In vitro invasion assays are performed using SU-ECM with normal human fibroblasts, keratinocytes, and endothelial cells as previously described (Livant et al., (2000) J. Clin. Invest. 105: 1537-1545). Undifferentiated, first or second passage human keratinocytes are obtained from the laboratory of C. Marcelo at the University of Michigan. Keratinocytes are cultured in serum-free keratinocyte growth medium (Clonetics, San Diego Calif.). Neonatal fibroblasts are obtained from the laboratory of J. Varani at the University of Michigan. First or second passage neonatal fibroblasts are cultured as previously described (Livant et al., (1995) Cancer Res. 55: 5085-5093). Normal human endothelial cells (microvascular cells) are obtained from the laboratory of D. Arenb erg at the University of Michigan. Microvascular cells are cultured as described (White et al., (2001) J. Immunol. 16: 5362-5366). Cells from single cell suspensions (made with 0.25% trypsin/EDTA from Gibco Life Technologies, Grand Island N.Y.) are rinsed, and briefly prebound to the following peptides (1, 3, 4, 5): Ac-PRCGVPDVAQF-NH$_2$ (SEQ ID NO:1) (from MMP-1), Ac-PRCGVPDVAEY-NH$_2$ (SEQ ID NO:2) (from MMP-7), Ac-PRCGNPDVANY-NH$_2$ (SEQ ID NO:3) (from MMP-2), Ac-PRCGVPDLGRFQ-NH$_2$ (SEQ ID NO:4) (from MMP-9). The testing of the peptides containing the C-to-S substitution is used to determine if invasion-promoting activities result from their interactions with the cysteine switch of inactive MMP-1. Thus, the effects on invasion of the corresponding 4 peptides containing the C-to-S substitution at the third position: Ac-PRSGVPDVAQF-NH$_2$ (SEQ ID NO:7), Ac-PRSGVPDVAEY-NH$_2$ (SEQ ID NO:8), Ac-PR SGNPDVANY-NH$_2$ (SEQ ID NO:9), and Ac-PR SGVPDLGRFQ-NH$_2$ (SEQ ID NO:10) is also assayed. To verify the lack of activity in the peptides containing the C-to-S substitution at the third position, peptides consisting of the arbitrarily scrambled sequences from the MMP-1, -7, -2, and -9 region propeptides listed above are also tested. Final peptide concentrations in the SU-ECM invasion assays will range from 2 to 60 ng per ml. These concentrations are derived from the dose response curve shown in FIG. 1 of Example 1. After prebinding to each of the peptides listed above, fibroblasts, endothelial cells, and keratinocytes are placed on SU-ECM invasion substrates in the appropriate media for 4 hours at 37° C., the time required to observe maximal invasion percentages (Livant et al., (1995) Cancer Res. 55: 5085-5093). Cellular viability in SU-ECM invasion assays are next determined, and are expected to range from 90% to 99% (Livant et al., (1995) Cancer Res. 55: 5085-5093). Invasion percentages are the ratio of the number of cells located in the blastocoelic cavities of SU-ECM invasion substrates to the total number of single cells adhering to them on their exterior and their interior surfaces. Each invasion percentage is the result of 3 to 4 independent determinations involving the scoring of the positions of all individual cells adhering to SU-ECM, typically about 100 individual cells for each determination.

Peptide synthesis. Peptides are synthesized using standard Fmoc/t-butyl protection strategies at 25 to 100 micromole scales on a Ranin Symphony multiple peptide synthesizer at the University of Michigan as previously described (Livant et al., (2000) J. Clin. Invest. 105: 1537-1545). The synthetic methods employed are a modification of the solid-phase method of Merrifield. Peptides are synthesized on a chlorotrityl resin and C-terminally amidated peptides are synthesized on Rink resin. The completed peptides are cleaved from the resin support and the side chain protecting groups simultaneously removed by anhydrous trifluoroacetic acid (TFA). The peptides are then precipitated with diethylether, purified by preparative HPLC, and lyophilized. Peptide purities are assessed by reverse phase HPLC, performed according to standard procedures, as previously described (Livant et al., (2000) J. Clin. Invest. 105: 1537-1545). Peptide structures are then confirmed by mass spectrometry and amino acid analysis as described (Livant et al., (2000) J. Clin. Invest. 105: 1537-1545). Because the presence of TFA, a very strong acid, could affect peptide activity in aqueous solution or injure the mice, residual TFA is removed by gel permeation chromatography as previously described (Schnaper et al., (1993) J. Cell. Physiol. 156(2): 235-246). Peptides are then lyophilized to remove the acetic acid and stored as lyophilized solids at −20° C. until soulobization in normal saline at concentrations of 1 to 5 mg per ml for use in vitro invasion assays, or as topical agents in db/db mouse wounds.

Use of function-locking antibodies in invasion assays The effects of function-blocking anti MMP 1 (COMY 4A2) antibody on Ac-PRCGVPDVAQF-NH$_2$ (SEQ ID NO:1) (MMP-1 switch peptide)-induced invasion is determined for keratinocytes, fibroblasts, and microvascular cells, placed on SU-ECM in vitro invasion substrates. To assess the specificity of the role of MMP-1 in switch peptide-induced invasion, the effects of function-blocking anti MMP 2 (CA 4001), and MMP 9 (GE 213) monoclonal antibodies (Schnaper et al., (1993) J. Cell. Physiol. 156(2): 235-246) are also determined. All of the antibodies are purchased from Chemicon International (Temecula Calif.). Antibodies are prebound to cells for 30 minutes on ice in concentrations ranging from 10 to 300 μg per ml, prior to their placement on invasion substrates, according to established procedures (Livant et al., (2000) J. Clin. Invest. 105: 1537-1545, 11, 25).

Western blotting and zymography. Confluent 100 mm dishes of fibroblasts, microvascular cells, and keratinocytes (each containing about 2 million cells) are treated with the appropriate peptides for 24 hours. Based on known procedures for Western blotting the media from cells treated with the other peptides, cells are treated with 10 μg/ml switch region prodomain peptide, serine-substituted peptide, or scrambled peptide per 20,000 cells. After treatment, cells are rinsed with PBS and lysed in ice-cold buffer (50 mM Tris-Cl pH 7.5, 150 mM NaCl, 2 mM EGTA, 1% Triton X-100) containing protease inhibitors (1× complete protease inhibitor cocktail, Roche). The lysate is collected and centrifuged at 12,000×g for 10 min at 4° C. and the resulting pellet resuspended in SDS-sample buffer (2% SDS (v/v), 62.5 mM Tris-HCl pH 6.8, 10% glycerol) with protease inhibitors and boiled at 100° C. for 5 min and centrifuged at 12,000×g for 10 min. The protein concentration in the resulting supernatant is determined by BCA microassay, using albumin standards also prepared in soulobization buffer. Prior to electrophoresis, samples are brought to 5% (v/v) 2-mercaptoethanol and incubated at 100° C. for 5 min. Approximately 30 μg of total protein per sample in SDS buffer is resolved on 10% polyacrylamine gels, and the separated proteins transferred onto polyvinylidene difluoride membranes (PVDF, Millipore, Bedford, Mass.). Membranes are blocked for 1 hour in 0.1% (v/v) Tween-20 in PBS (PBS-T) containing 5% (w/v) nonfat dry milk prior to antibody binding. Membranes are then incubated for 1 hour at room temperature with antibodies at a dilution of approximately 1:5000 in blocking solution. Then, membranes are incubated for 1 hour with goat anti-mouse IgG antibody conjugated to horseradish peroxidase (Jackson Immunoresearch Labs, West Grove, Pa.) at a dilution of 1:5000 in blocking solution. The membranes are processed for detection by enhanced chemiluminescence (ECL reagent, Amersham, Arlington Heights, Ill.). The amount of cellular MMP in each band will be quantified using Quantity One software (Bio-Rad, Hercules, Calif.) by comparing to the corresponding recombinant MMP standard curve generated from the same blot. For zymography, adherent cells and their media

EXAMPLE 4

Testing the Effects of the MMP 1 Cysteine Switch Peptide on Dermal Wound Healing in Obese Diabetic Mice and in Their Heterozygous, Non-diabetic Littermates Biopsy punches 4 mm in diameter (Henry Schein, Inc., Port Washington N.Y.) are used to wound C57B16 KsJ db/db and C57B16KsJ db/+ mice as previously described (Livant et al., (2000) J. Clin. Invest. 105: 1537-1545). Db/db mice and their non-diabetic, db/+ littermates are obtained at 6 to 8 weeks of age from Jackson Laboratories (Bar Harbor Me.).

Db/db mice are aged at least an additional 2 weeks prior to use in wound healing experiments, to make certain that they display the impaired wound healing phenotype characteristic of this strain. Treatment groups consist of 10 to 20 dermal wounds each, or 5 to 10 db/db or db/+ mice with duplicate dermal wounds. Anesthetized mice are wounded once or twice on the upper back by pinching the skin away from the underlying fascia and muscle, and pushing the biopsy punch through the skin as it lies over a forefinger. When wounded without penetrating the fascia or underlying muscle, bleeding is not apparent in dermal wounds in db/db and db/+ mice (Livant et al., (2000) J. Clin. Invest. 105: 1537-1545). Thus, added peptide is not expected to be significantly diluted as it is delivered to wounds. As previously judged by measuring sections of day-old wounds with a reticle at 400-fold magnification (Livant et al., (2000) J. Clin. Invest. 105: 1537-1545), db/db mice are expected to be wounded to a mean depth of approximately 1.7 mm by this procedure. The depth of the wounds in the db/+ mice is expected to be somewhat less because of the reduced amount of subcutaneous fat in these animals. However, in no case is underlying muscle wounded. In each experiment, the mice are age-matched. Based on preliminary dose response studies with the MMP-7 switch region propeptide, approximately 10 µg of the Ac-PRCGVPDVAQF-NH$_2$ (SEQ ID NO:1) peptide from MMP-1 proprotein switch region is added to wounds in a volume of 5 µl normal saline (NS). The corresponding peptide containing the C-to-S substitution at the third position, Ac-PRSGVPDVAQF-NH$_2$ (SEQ ID NO:7) is also assessed for its ability to promote db/db wound healing. To verify the lack of activity in the peptide containing the C-to-S substitution at the third position, a peptide consisting of the scrambled sequence from the MMP-1 proprotein switch region, Ac-VVDAPPFCGQR-NH$_2$ (SEQ ID NO:11) is also tested. To assess the locality of the effect of switch region propeptide treatment on dermal wound healing, some db/db and db/+ mice receive peptide in only 1 of 2 duplicate wounds; while the remaining wound on each mouse receive 5 µl of NS only. This strategy has been previously used to demonstrate the locality of PHSRN-mediated wound healing enhancement in db/db mice (Livant et al., (2000) J. Clin. Invest. 105: 1537-1545).

EXAMPLE 5

Histological Analysis of Wound Reepithelialization and Provisional Matrix Formation On day 0, 27 aged db/db mice or db/+ mice are wounded in duplicate with a 4 mm biopsy punch as described above. Mice are divided into 3 treatment groups of 8 mice. The wounds of each group are treated once with 5 µl NS containing either 10 µg Ac-PRCGVPDVAQF-NH$_2$ (SEQ ID NO:1) (from MMP-1), Ac-PRSGVPDVAQF-NH$_2$ (SEQ ID NO:7) (the corresponding C-to-S mutant sequence, or NS. On days 1 through 9, a mouse from each treatment group is sacrificed. Its wounds are dissected out, each surrounded by unwounded skin. Thus, all the wounded mice are assayed in this experiment. Wounds are fixed for at least 3 days in 5% formaldehyde in PBS, and embedded in paraffin.

Prior to sectioning and staining with hematoxylin and eosin according to standard procedures (Schnaper et al., (1993) J. Cell. Physiol. 156(2): 235-246), the blocks are cut to expose the wounded tissue near the center of each wound. For each wound, the distance migrated from the wound edges by keratinocytes is measured in 5 groups of 3 serial 5-micron sections. Fifty sections, or 250 microns separate each group of 3 serial sections from the next group. The distance migrated is measured using a reticle and a standard grid with phase contrast optics at 100-fold and at 250-fold magnification. The entire wound bed or new dermal tissue is also examined in each section of each wound at 200 and 400-fold magnification. Macrophages in the provisional matrix (as recognized by their eosinophilic cytoplasm, large, euchromatic nuclei, and ruffled cell membrane) are counted, and the presence of activated fibroblasts (as demonstrated by their lightly staining, euchromatic nuclei and extensive, basophilic cytoplasm) is scored. The presence of thick type I collagen fibers in the provisional matrix, characteristic of contracting wounds, is also evaluated for each treatment group. These histological assays are performed as previously described (Livant et al., (2000) J. Clin. Invest. 105: 1537-1545).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

I claim:

1. A method for treating a wound, comprising:
   a) providing
      i) an MMP prodomain peptide, wherein said peptide has an amino acid sequence selected from the group consisting of Ac-PRCGVPDVAQF-NH$_2$, Ac-PRCGVPDVAEY-NH$_2$, Ac-PRCGNPDVANY-NH$_2$, and Ac-PRCGVPDLGRFQ-NH$_2$: and
      ii) a subject having at least one wound; and
   b) administering said peptide to said subject under conditions such that the healing of said wound is promoted.

2. The method of claim 1, wherein said subject is a patient with diabetes.

3. The method of claim 1, wherein said subject is a burn patient.

4. The method of claim 1, wherein said wound is a chronic wound.

5. A kit for the treatment of wounds in a subject, comprising
   a) an MMP prodomain peptide, wherein said peptide has an amino acid sequence selected from the group consisting of Ac-PRCGVPDVAQF-NH$_2$, Ac-PRCGVPDVAEY-NH$_2$, Ac-PRCGNPDVANY-N$_2$, and Ac-PRCGVPDLGRFQ-NH$_2$; and
   b) instruction for using said peptide to treat said wounds in said subject.

6. The kit of claim 5, wherein said subject is a patient with diabetes.

7. The kit of claim 5, wherein said subject is a burn patient.

8. The kit of claim 5, wherein said wound is a chronic wound.

* * * * *